United States Patent [19]

Heumüller et al.

[11] Patent Number: 5,319,131

[45] Date of Patent: Jun. 7, 1994

[54] α-FLUOROACRYLIC ACID ESTERS AND POLYMERS THEREOF

[75] Inventors: Rudolf Heumüller, Bad Soden an Taunus; Günter Siegemund, Hofheim am Taunus; Werner Groh, Frankfurt am Main; Gerhard Wieners, Frankfurt Am Ma, Peter Herbrechtsmeier, Königstem/Taunus, all of Fed. Rep. of Germany

[73] Assignee: Hoechst Aktiengesellschaft, Frankfurt am Main, Fed. Rep. of Germany

[21] Appl. No.: 21,282

[22] Filed: Feb. 22, 1993

Related U.S. Application Data

[60] Division of Ser. No. 837,768, Feb. 18, 1992, Pat. No. 5,198,925, which is a continuation of Ser. No. 886,114, Jul. 16, 1986, abandoned.

[51] Int. Cl.$^5$ .............................. C07C 69/62
[52] U.S. Cl. ...................... 560/219; 560/211; 582/862
[58] Field of Search ............ 562/862; 560/219, 211

[56] References Cited

U.S. PATENT DOCUMENTS

| | | | |
|---|---|---|---|
| 3,177,185 | 4/1965 | Hollander et al. | 560/223 |
| 3,359,066 | 12/1967 | Hatch et al. | 359/356 |
| 3,486,805 | 12/1969 | Kobayashi | 359/356 |
| 3,724,934 | 4/1973 | Bloom | 359/356 |
| 3,823,171 | 7/1974 | Pittmann et al. | 260/408 |
| 4,259,407 | 3/1981 | Tada | 428/421 |
| 4,297,466 | 10/1981 | Block et al. | 526/218 |
| 4,323,695 | 4/1982 | Bloch et al. | 562/862 |
| 4,328,318 | 5/1982 | Miranday et al. | 359/356 |
| 4,863,236 | 9/1989 | Herbrechtsmeier et al. | 526/204 |
| 5,000,547 | 3/1991 | Squire | 359/642 |

FOREIGN PATENT DOCUMENTS

| | | | |
|---|---|---|---|
| 128516 | 12/1984 | European Pat. Off. | |
| 0128517 | 12/1984 | European Pat. Off. | |
| 1115287 | 5/1968 | United Kingdom | |
| 8700297 | 1/1987 | World Int. Prop. O. | 359/642 |

OTHER PUBLICATIONS

Abstract: 93:150886c–Transparent poly(phenyl d--fluorocarbylate-'80.

*Primary Examiner*—Paul J. Killos

[57] ABSTRACT

Esters of α-fluoroacrylic acid are accessible by hydrolysis of an α-hydroxymethyl-α-fluoromalonic acid ester, decarboxylation and dehydration of the hydrolysis product and subsequent esterification of the resulting α-fluoroacrylic acid with an alcohol. The esters are polymerizable and are suitable for use as a starting material for preparing fluoropolymers which in turn are usable as materials for manufacturing transparent articles. The polymers are high-molecular and non-crystalline and have softening temperatures of above 100° C.

12 Claims, No Drawings

α-FLUOROACRYLIC ACID ESTERS AND POLYMERS THEREOF

This is a division of our copending application U.S. Ser. No. 07/837,768, filed Feb. 18, 1992, now U.S. Pat. No. 5,198,925, issued Mar. 30, 1993, which is a continuation of copending application U.S. Ser. No. 06/886,114, filed Jun. 16, 1986, now abandoned.

The invention relates to a-fluoroacrylic acid esters and polymers thereof, to a process for preparing α-fluoroacrylic acid esters and polymers thereof, and to the use of these polymers.

Esters of a-fluoroacrylic acid are already known. For instance, the phenyl ester of a-fluoroacrylic acid is prepared by reacting ethyt monofluoroacetate with ethyl oxalate in the presence of sodium ethylate, converting the resulting sodium a-fluoroacrylate with thionyl chloride into α-fluoroacryloyl chloride, and then esterifying the latter with phenol (German Patent 2,950,491 = U.S. Pat. No. 4,297,466). It is disadvantageous herein that the highly toxic ethyl monofluoroacetate must be used. Phenyl α-fluoroacrylate is polymerizable and serves for preparing polymers which at room temperature are transparent, i.e. see-through or light-transmitting, and colorless solids.

Further esters of a-fluoroacrylic acid, in particular butyl α-fluoroacrylate, are preparable by acid hydrolysis of the respective α-hydroxymethyl-α-fluoromalonate and subsequent decarboxylation of the hydrolysis product with simultaneous elimination of alcohol (British Patent 1,115,287). However, this method has only been described for the example of butyl α-fluoroacrylate; the ester polymerizes rapidly on exposure to light.

It is further known that polymers of a-halogenoacrylic acid esters with halogen-containing alcohol components serve for preparing radiation-sensitive protective layers (U.S. Pat. No. 4,259,407). The starting materials used are monomers of the formula $H_2C=CX\text{-}COOR$, in which X is a fluorine, chlorine or bromine atom and R represents a fluorinated alkyl, aryl or alkoxy group. Of the polymers which contain only fluorine as the halogen, poly(trifluoroisopropyl α-fluoroacrylate) is mentioned as an example; however, no information is provided about any properties of this polymer or of the corresponding monomer.

Finally, European Application Publication 0,128,517 discloses an optical material which comprises a polymeric α-fluoroacrylic acid ester which may contain deuterium atoms not only on the β-carbon atom of the vinyl group but also in the alcohol component. These polymers serve as a core material for optical fibers; they have a molecular weight of 200,000 to 5,000,000 (gel permeation), a refractive index of 1.45 to 1.60 and a softening temperature of 100° to 200° C. The sheath material of the optical fibers is made of polymers which have a lower refractive index; suitable for this purpose are for example polymers of a-fluoroacrylic acid esters whose alcohol component contains fluorine atoms, for example trifluoroethyl α-fluoroacrylate and hexafluoroisobutyl α-fluoroacrylate.

The preparation and properties of the aforementioned poly(fluoroalkyl α-fluoroacrylates) have likewise been described (European Application Publication 0,128,516). The polymers are obtained by free-radical initiated polymerization of the monomers in bulk, solution or suspension in the presence of a chain transfer agent at a temperature of 0° to 100° C. The polymers have a molecular weight of 200,000 to 5,000,000 (gel permeation), a refractive index of 1.36 to 1.44 and a softening temperature of 80° to 140° C.

The invention has for its object to provide esters of α-fluoroacrylic acid with a highly fluorinated alcohol radical and the corresponding polymers which can be processed into articles of high transparency.

The invention provides α-fluoroacrylic acid ester of the formula (1)

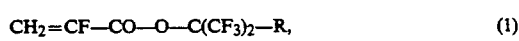

$$CH_2=CF\text{-}CO\text{-}O\text{-}C(CF_3)_2\text{-}R, \quad (1)$$

in which R denotes a hydrogen atom, a deuterium atom, a halogen atom, an aliphatic radical having 1 to 4 carbon atoms or an aromatic radical having 4 to 10 carbon atoms; this is, for example, hexafluoroisopropyl α-fluoroacrylate of the formula (2)

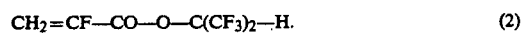

$$CH_2=CF\text{-}CO\text{-}O\text{-}C(CF_3)_2\text{-}H. \quad (2)$$

The invention further provides a process for preparing an α-fluoroacrylic acid ester, which comprises reacting in a first process step dimethyl α-fluoromalonate with formaldehyde, then in a second process step subjecting the resulting hydroxymethylated dimethyl α-fluoromalonate to hydrolysis, decarboxylation and dehydration and subsequently, in a third process step, esterifying the resulting α-fluoroacrylic acid, if desired in the form of an acid halide, with an alcohol of the formula (3)

$$HO\text{-}C(CF_3)_2\text{-}R, \quad 3)$$

in which R has the meaning indicated in the case of formula (1), if desired in the form of an alkali metal alcoholate.

The invention also provides a fluorine-containing polymer which is essentially composed of monomer units which are derived from an α-fluoroacrylic acid ester òf the formula (1).

The invention additionally provides a process for preparing a fluorine-containing polymer by free-radical initiated polymerization of a fluorine-containing monomer, which comprises polymerizing an α-fluoroacrylic acid ester of the formula (1), if desired in mixture with another, copolymerizable vinyl compound, at a temperature of 60° to 150° C.

The invention finally also provides the use of a fluorine-containing polymer which is essentially composed of monomer units which are derived from an α-fluoroacrylic acid ester of the formula (1) as a material for preparing transparent articles.

The process according to the invention for preparing an α-fluoroacrylic acid ester is carried out in three stages. First dimethyl α-fluoromalonate is reacted with formaldehyde to give dimethyl a-hydroxymethyl-α-fluoromalonate, which is then hydrolyzed and the hydrolysis product is dicarboxylated and dehydrated, and finally the resulting α-fluoroacrylic acid is esterified with an alcohol of the formula (3).

In the first process step, dimethyl α-fluoromalonate is subjected to a hydroxymethylation with formaldehyde. (Dimethyl α-fluoromalonate is a known compound; see Journal of Fluorine Chemistry 25 (1984), 203–212.) The formaldehyde is preferably used in the form of an aqueous solution which has a formaldehyde content of 30 to 40 percent by weight. The formaldehyde is used in an amount of 1 to 10 moles, preferably 1.1 to 3 moles (based on 1 mole of dimethyl α,-fluoromalonate). Instead of formaldehyde, it is also possible to use paraformaldehyde, hexamethylenetetramine or 1,3,5-trioxane. It is advantageous to carry out the reaction in the presence of a basic catalyst which is then used in an amount of 2 to 50, preferably 5 to 15, mol % (based on dimethyl α-fluoromalonate). The catalyst used is in particular an alkali metal hydrogencarbonate, for example potassium hydrogencarbonate and sodium hydrogencarbonate. The reaction is carried out at a temperature of 5° to 40° C., preferably of 15° to 30° C. The resulting dimethyl ester of α-hydroxymethyl-α-fluoromalonic acid is then isolated out of the reaction mixture, preferably by salting out or extraction by means of a water-nonmiscible organic solvent. A suitable solvent is in particular an aliphatic chlorohydrocarbon having 1 to 4 carbon atoms, for example dichloromethane, trichloromethane, tetrarhloromethane, 1,1-dichloroethane, 1,2-dichloroethane. A combination of salting out and extraction is particularly advantageous; therein the reaction mixture has first added to it a saturated salt solution (ammonium sulfate, sodium chloride), and this mixture is then extracted. By evaporating the solvent, α-hydroxymethyl-α-fluoromalonic acid is obtained as a colorless solid.

In the second process step the dimethyl ester of α-hydroxymethyl-α-fluoromalonic acid is hydrolysed in aqueous acid medium, and the hydrolysis product is decarboxylated and dehydrated. The reaction is carried out at a pH value of −1 to 6, preferably 0 to 2; the acid medium is prepared by means of an aqueous acid solution, preferably of a dilute inorganic acid such as hydrochloric acid or sulfuric acid. The reaction temperature is within the range from 90° to 110° C., preferably 95° to 105° C. After the gas evolution has ended, the reaction mixture is distilled under a pressure of 1013 to 600 mbar, and the distillate is extracted with an organic solvent. The solvent used here is likewise a water-nonmiscible solvent, preferably an ether such as diethyl ether. Evaporation of the solvent leaves α-fluoroacrylic acid as a colorless solid. In a preferred variant, the α-fluoroacrylic acid is isolated as an ammonium salt. To this end, gaseous ammonia is passed through the solution obtained after the extraction., and the colorless crystalline precipitate is then freed of solvent.

In the third process step, the α-fluoroacrylic acid is esterified with an alcohol of the formula (3). The alcohol is used in an amount of 0.5 to 2 moles, preferably 0.8 to 1.2 moles (based on 1 mole of α-fluoroacrylic acid). For the esterification the α-fluoroacrylic acid is used as such or preferably in the form of an acid halide, in particular as a-fluoroacryloyl chloride. The acid halide is prepared by means of a customary halogenating agent, for example oxalyl chloride, phosphorus pentachloride, phosphorus trichloride, phosphorus oxychloride, benzoyl chloride, benzotrichloride, phosphorus tribromide, sulfur tetrafluoride and in particular thionyl chloride. The halogenation with thionyl chloride is preferably effected in the presence of a catalyst such as dimethylformamide. The reaction is carried out in an aromatic hydrocarbon, for example toluene, xylene and trimethylbenzene, as solvent, and the reaction temperature is within the range from 50° to 100° C., preferably 70° to 90° C. The esterification is likewise carried out in a solvent, and the reaction temperature is here 0° to 30° C., preferably 5° to 25° C. Suitable solvents are aliphatic, alicyclic or aromatic hydrocarbons, for example n-hexane, n-heptane, cyclohexane, methylcyclohexane, benzene, toluene, xylene and mesitylene, and also symmetrical, asymmetrical or cyclic ethers, for example diethyl ether, dipropyl ether, diisopropyl ether, tert.-butyl methyl ether, diethylene glycol dimethyl ether, tetrahydrofuran and dioxane, as well as aliphatic or aromatic halohydrocarbons, preferably chlorohydrocarbons, for example dichloromethane, trichloromethane, tetrachloromethane, 1,1-dichloroethane, 1,2-dichloroethane, chlorobenzene and 1,2-dichlorobenzene, and even aliphatic or aromatic nitrites, for example acetonitrile and benzonitrile. It is expedient to carry out the esterification of the acid halide in the presence of an organic base, in particular a trialkylamine having 1 to 4 carbon atoms in each of the alkyl groups, for example triethylamine, triisopropylamine and tributylamine. The base is used in an amount of 0.5 to 2 moles, preferably 0.8 to 1.2 moles (based on 1 mole of α-fluoroacrylic acid). The resulting α-fluoroacrylic acid ester is isolated from the reaction mixture by distillation, preferably under a pressure of 200 to 1013 mbar. The distillation is expediently carried out in the presence of 100 to 500 ppm of a commercially available polymerization inhibitor, for example hydroquinone or hydroquinone monomethyl ether. Purification is effected by renewed distillation or recrystallization.

To esterify the α-fluoroacrylic acid ester. use is made of an alcohol of the formula (3)

$$HO-C(CF_3)_2-\quad\quad\quad (3)$$

in which R denotes a hydrogen atom, as deuterium atom, a halogen atom (preferably a fluorine atom), an aliphatic radical (preferably an alkyl radical which may have deuterium atoms or fluorine atoms) having 1 to 4 carbon atoms or an aromatic radical (preferably a phenyl radical which may be substituted by one or more halogen atoms or one or more lower alkyl or alkoxy radicals) having 4 to 10 carbon atoms. Suitable alcohols are, for example 1,1,1,3,3,3-hexafluoro-2-propanol, 1,1,1,3,3,3-hexafluoro-2-propanol-$D_2$, perfluoro-2-propanol, perfluoro-tert.-butanol, perfluoro-1,1-dimethylpropanol, 1,1,1,3,3,3-hexafluoro-2-methyl-2-propanol, 1,1-bis(trifluoromethyl)propanol, 1,1-bis(trifluoromethyl)Propanol-$D_5$, 1,1,1,3,3,3-hexafluoro-2-methyl-2-propanol, perfluoro-2,3-dimethyl-2-butanol, hexafluoro-2-phenyl-2-propanol, hexafluoro-2-(4-fluorophenyl)-2-propanol, hexafluoro-2-(3,4-dimethylphenyl)-2-propanol, hexafluoro-2-(4-methoxyphenyl)-2-propanol, hexafluoro-2-(2-furyl)-2-propanol, hexafluoro-2-(2-thienyl)-2-propanol. The alcohol is used if desired in the form of an alkali metal alcoholate, preferably a sodium alcoholate or potassium alcoholate.

The α-fluoroacrylic acid esters according to the invention are colorless liquids or solids at room temperature. They are polymerizable and are suitable for use as starting materials for preparing fluoropolymers. They are also copolymerizable with other vinyl compounds. Such particularly suitable vinyl compounds are esters of methacrylic acid and esters of α-fluoroacrylic acid, preferably alkyl esters of methacrylic acid and alkyl esters of α-fluoroacrylic acid having in each case 1 to 6 carbon atoms in the alkyl radical. Examples thereof are in particular methyl methacrylate and methyl α-fluoroacrylate. The weight ratio of α-fluoroacrylic acid ester to the other vinyl compounds used as comonomers is in general 60:40 to 99:1, preferably 65:35 to 75:25.

The polymerization is carried out in conventional manner, preferably in bulk , by means of a free-radical initiator. Suitable initiators are for example azo compounds such as azobisisobutyronitrile and organic peroxides such as tert.-butyl peroxide, tert.-butyl peroctoate, tert.-butyl peroxyisopropylcarbonate, tert.-butyl hydroperoxide and tert.-butyl peroxyisobutyrate. The amount of initiator is within the range from 0.01 to 3, preferably 0.03 to 0.3, moles per 100 moles of the monomer(s). It is advantageous to carry out the polymerization in the presence of a chain transfer agent (regulator). Suitable for this purpose are in particular mercaptans such as butylmercaptan, tert.-butylmercaptan, propylmercaptan, phenylmercaptan and tert.-hexylmercaptan and also esters of mercaptoacetic acid, for example ethyl mercaptoacetate and ethylene glycol bis(mercaptoacetate). The polymerization temperature is 60° to 150° C., preferably 80° to 130° C.

It is advisable to degas the reaction mixture before the start of the polymerization. To this end, the reaction mixture of monomers, initiator and, if used, regulator is first cooled down in a reactor to a temperature of at least $-100°$ C., and the reactor is then evacuated and, white in the seated state, is warmed to a temperature of 0° to 25° C.; this process can be repeated several times.

The polymer according to the invention is produced in the form of a glass-clear material which is thermoplastically moldable. It is therefore suitable in particular for use as a material for manufacturing transparent articles, for example resist materials, lenses and optical fibres The spectral transmittance of the polymer is particularly high within the wavelength range from 600 to 1300 nm. The polymer has the following characteristic properties:

Average molecular weight 8,000 to 5,000,000, preferably 10,000 to 200,000 (measured by the light-scattering method); glass transition temperature: 95° to 150° C., preferably 100° to 145° C.; decomposition temperature: at least 230° C., preferably 250° to 300° C.

The examples below serve to illustrate the invention in more detail. The percentages are by weight.

EXAMPLE 1 a) 48 g (0.48 moo of potassium hydrogencarbonate are dissolved in 535 g (6.59 moo of aqueous formaldehyde solution (37 percent by weight) in a 4-liter glass flask. To this solution were added dropwise with stirring 841 g (5.6 mol) of dimethyl α-fluoromalonate in the course of 3½ hours, during which the temperature was maintained in the range from 20° to 25° C. During further stirring at the same temperature for 2 hours, the dimethyl ester of α-hydroxymethyl-α-fluoromalonic acid precipitated as a colorless solid. To the reaction mixture were then added 2500 g of an aqueous saturated ammonium sulfate solution, which was followed by extraction with dichloromethane. The extraction solution was dried with anhydrous sodium sulfate. Removal of the dichloromethane by distillation (bath temperature 40° C., 25 mbar) left 906 g (90 percent of theory) of dimethyl α-hydroxymethyl-α-fluoromalonate.

Elemental analysis gave the following values (in percent):

| calculated: | C | 40.0 | H | 5.04 | F | 10.54 | O | 44.4 |
|---|---|---|---|---|---|---|---|---|
| found: | | 39.9 | | 5.1 | | 10.4 | | 44.6 | b) 175 g (0.97 mol) of dimethyl α-hydroxymethyl-α-fluoromalonate, 750 ml of water and 750 ml of hydrochloric acid (36 percent by weight) were heated to the boiling point for 2 1/2 hours in a 2-liter glass flask which had been equipped with a thermometer and a stirrer and via a Vigreux column with a distillation attachment.

Therein the temperature of the reaction mixture was 1030C. The reaction mixture was then distilled. The distillate was treated with 1 g of hydroquinone monomethyl ether and extracted with diethyl ether, and the extraction solution was dried with anhydrous sodium sulfate. 17 g (1 moo of gaseous ammonia were then passed at room temperature into the solution. The resulting colorless precipitate was filtered off, was washed with diethyl ether and was dried at room temperature and under reduced pressure. 70.8 g (68 percent of theory) of ammonium α-fluoroacrylate were obtained.

Elemental analysis gave the following values (in percent):

| calculated: | C | 33.6 | H | 5.6 | F | 17.7 | N | 13.1 | O | 29.9 |
|---|---|---|---|---|---|---|---|---|---|---|
| found: | | 33.3 | | 5.6 | | 17.8 | | 13.1 | | 29.9 | c) A 2-liter glass flask which had been equipped with a thermometer.- a stirrer, a reflux condenser and a dropping funnel was charged with 1.2 l of o-xylene, 29 g (0.4 mol) of dimethylformamide and 200 g (1.87 mol) of ammonium α-fluoroacrylate. To this initial charge were then added dropwise in the course of 1 hour 238 g (2.0 mol) of thionyl chloride. The reaction mixture was then maintained at a temperature of 80° C. for 2 hours. After subsequently cooling down to a temperature of 0° C., the mixture had added to it a mixture of 202 g (2 mol) of triethylamine and 336 g (2 mol) of hexafluoroisopropanol in the course of 30 minutes. The resulting mixture was stirred for a further 30 minutes, and the resulting precipitate was filtered off. The filtrate was treated with 1 g of hydroquinone monomethyl ether and rapidly distilled under a pressure of 266 mbar. The fraction obtained within the temperature range from 45° to 85° C. was washed with hydrochloric acid (2.4 molar) and with water, was dried and was distilled again, giving 232 g (52 percent of theory) of pure hexafluoroisopropyl α-fluoroacrylate.

This ester was a colorless liquid with a refractive index $n_D^{23} = 1.3145$ a boiling point of 46.8° C. (at 213 mbar) and a density of 1.453 g/cm³ (at 25° C.). In the wavelength range from 380. to 680 nm this ester had an average transmission of more than 99 percent.

Identification was effected by means of the ¹H-NMR spectrum (with tetramethylsilane as the standard) and the ¹⁹ F-NMR spectrum (trifluoromethane as the standard); deuterochloroform was used as the solvent. The compound of the formula

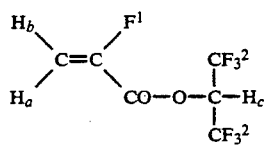

was found to have the following chemical shifts (δ) and coupling constants (j):

| $\delta H_a$ = 5.89 | $J_{H_aH_b}$ = 3.75 hertz |
|---|---|
| $\delta H_b$ = 5.60 | $J_{H_aF}$ = 41.4 hertz |
| $\delta H_c$ = 5.81 | $J_{H_bF}$ = 12.2 hertz |

-continued

| | |
|---|---|
| $\delta F^1 = 118.02$ | $J_{H_cF} = 6.1$ hertz |
| $\delta F^1 = 73.78$ | |

The elemental composition of the compound was determined by means of high-resolution mass spectrometry:
calculated: M+ =240.0021; found: M+ =240.0029 m/e

EXAMPLE 2 a) 150 g (1 mol) of dimethyl α-fluoromalonate were added dropwise at 25° C. in the course of an hour to a mixture of 96 g of 35 percent by weight strength aqueous solution of formaldehyde (1.1 mol) and 10 g (0.1 mol) of potassium hydrogencarbonate. The reaction solution was then mixed with four times the volume of a saturated aqueous ammonium sulfate solution, and the mixture was extracted three times with 150 ml of dichloromethane each time. The combined extraction solutions were dried over sodium sulfate. Evaporating the dichloromethane left dimethyl αa-hydroxymethyl-α-fluoromalonate behind as a colorless solid.

b) 180 g (1 mol) of dimethyl α-hydroxymethyl-α-fluoromalonate were heated to the boiling point in 1.5 liters of 6 N hydrochloric acid for 2.5 hours, thereby undergoing dehydration and decarboxylation. After gas evolution had ended, the reaction mixture was distilled under a pressure of 700 mbar, and the distillate was extracted three times with 150 ml of diethyl ether each time. The combined extraction solutions were dried over sodium sulfate. On passing 19 g (1.1 mol) of gaseous ammonia into the ether solution the ammonium salt of α-fluoroacrylic acid was obtained as a colorless solid.

c) 107 g (1 mol) of the ammonium salt of α-fluoroacrylic acid were mixed with 14.5 g (0.2 mol) of dimethylformamide and 0.6 l of xylene, and to the mixture were added dropwise in the course of one hour 131 g (1.1 mol) of thionyl chloride; the mixture was then heated at a temperature of 80° C. for two hours. After cooling down to a temperature of 0° C., the reaction mixture had added to it in the course of 30 min a mixture of 204 g (1.1 mol) of tributylamine and 185 g (1.1 mol) of hexafluoroisopropanol. The mixture was then stirred at a temperature of 30° C. for an hour and finally filtered. The filtrate was distilled under a pressure of 270 mbar, and the hexafluoroisopropyl ester of α-fluoroacrylic acid was obtained as a colorless liquid.

EXAMPLE 3

Example 2 was repeated using in section c) in place of 185 g of hexafluoroisopropanol now 187.1 g (1.1 mol) of dideuterohexafluoroisopropanol.

Distillation under a pressure of 213 mbar gave 132.5 g (50 percent of theory) of deuterohexafluoroisopropyl α-fluoroacrylate as a colorless liquid having a boiling point of 47° C.

EXAMPLE 4 a) In a 1-liter glass flask, 100 g (0.934 mol) of ammonium α-fluoroacrylate (obtained according to Example 1) were dispersed in a mixture of 600 g of mesitylene and 15 ml of dimethylformamide, and 119 g (1.0 mol) of thionyl chloride were added in the course of one hour. The resulting mixture was heated to a temperature of 80° C. and maintained at this temperature with stirring for 2 hours. The liquid obtained on cooling down to room temperature was distilled under reduced pressure, and the fraction obtained up to 100° C./160 mbar was distilled once more under atmospheric pressure. 67 g (66 percent of theory) of α-fluoroacryloyl chloride having a boiling point of 65° to 67° C. were obtained.

b) 15.3 g (0.092 mol) of hexafluoroacetone were passed with stirring in the course of 30 minutes at a temperature of 25° C. into a suspension of 5.34 g (0.092 mol) of dried potassium fluoride in 25 ml of dry diethylene glycol dimethyl ether, and the potassium fluoride dissolved. After a further 2 hours of stirring, unreacted hexafluoroacetone was distilled off under reduced pressure (water jet pump). 10 g (0.092 mol) of α-fluoroacryloyl chloride were added at a temperature of 25° C. with stirring to the remaining solution in the course of 5 minutes, and a colorless solid precipitated. The reaction mixture was stirred at a temperature of 25° C. for a further 80 minutes, and 0.005 g of hydroquinone monomethyl ether were then added, which was followed by distillation under a pressure of 40 mbar. 17.6 g (74 percent of theory) of perfluoroisopropyl α-fluoroacrylate having a boiling point of 40° C. (under 165 mbar) were obtained.

EXAMPLE 5

A solution of 213.6 g (0.571 mol) of potassium perfluoro-2,3-dimethyl-2-butanolate in 250 ml of dry diethyl ether was added dropwise with stirring at a temperature of 25°0 C. to a solution of 62 g (0.571 mol) of α-fluoroacryloyl chloride (obtained according to Example 4) in 100 ml of dry diethyl ether in the course of 1 hour, and a colorless solid precipitated. The reaction mixture was stirred at a temperature of 25° C. for a further hour, and the solid was filtered off. The filtrate had added to it 0.01 g of hydroquinone monomethyl ether and was then distilled under reduced pressure. 167 g (72 percent of theory) of perfluoro-2,3-dimethyl-2-butyl α-fluoroacrylate having a boiling point of 43° C. (under 20 mbar) were obtained.

EXAMPLE 6

A mixture of 50 g (0.205 mol) of 2-phenylhexafluoroisopropanol and 20.8 g (0.205 mol) of triethylamine was added dropwise with stirring at a temperature of 25° C. to a solution of 22.5 g (0.207 mol) of α-fluoroacryloyl chloride (obtained according to Example 4) in 100 ml of dry dichloromethane in the course of 20 minutes. The reaction mixture was then maintained at a temperature of 45° C. for 90 minutes. After cooling down the mixture to 25° C. the resulting solid was filtered off. The filtrate was distilled under reduced pressure after addition of 0.005 g of hydroquinone monomethyl ether. 38.3 g (58 percent of theory) of 2-phenylhexafluoroisopropyl α-fluoroacrylate having a boiling point of 66° C. (under 5 mbar) were obtained.

EXAMPLE 7

A solution of 40 g (0.153 mol) of 2-(4-fluorophenyl)-hexafluoro-2-propanol and 15.5 g (0.153 mol) of triethylamine in 75 ml of dry diethyl ether were added dropwise with stirring at a temperature of 25° C. to a solution of 18 g (0.166 mol) of α-fluoroacryloyl chloride (obtained according to Example 4) in 25 ml of dry diethyl ether in the course of 45 minutes. The reaction mixture was then stirred at a temperature of 25° C. for a further 2 hours. The resulting solid was filtered off. The filtrate was distilled under reduced pressure after addition of 0.01 g of hydroquinone monomethyl ether. 42.5 g (83 percent of theory) of 2-(4-fluorophenyl)-hexafluoro-2-propyl α-fluoroacrylate having a boiling point of 70° to 73° C. (under 0.5 mbar) were obtained.

EXAMPLE 8

A solution of 21.5 g (0.067 mol) of 2-(4-bromophenyl)-hexafluoro-2-propanol and 6.8 g (0.067 mol) of triethylamine in 25 ml of dry diethyl ether was added dropwise with stirring at a temperature of 20° C. to a solution of 8.7 g (0.08 mol) of α-fluoroacryloyl chloride (obtained according to Example 4) in 25 ml of dry diethyl ether in the course of 30 minutes. The reaction mixture was then stirred at a temperature of 20° C. for a further 3.5 hours. The resulting solid was filtered off. The filtrate was distilled under reduced pressure after addition of 0.005 g of hydroquinone monomethyl ether. 18.8 g (71 percent of theory) of 2-(4-bromophenyl)-hexafluoro-2-propyl α-fluoroacrylate having a boiling point of 66° to 69° C. (under 0.13 mbar) were obtained.

EXAMPLE 9

A solution of 21 g (0.081 mol) of 2-tolylhexafluoro-2-propanol and 8.2 g (0.08 mol) of triethylamine in 25 ml of dry diethyl ether was added dropwise with stirring at a temperature of 20° C. to a solution of 9.8 g (0.09 mol) of α-fluoroacryloyl chloride (obtained according to Example 4) in 25 ml of dry diethyl ether in the course of 40 minutes. The reaction mixture was then stirred at a temperature of 20° C. for a further 4 hours. The resulting solid was filtered off. The filtrate was distilled under reduced pressure after addition of 0.02 g of hydroquinone monomethyl ether. 19.6 g (73 percent of theory) of 2-tolylhexafluoro-2-propyl α-fluoroacrylate having a boiling point of 58° to 60° C. (under 0.27 mbar) were obtained.

EXAMPLE 10

A solution of 27.3 g (0.1 mol) Of 2-(3,4-dimethylphenyl)hexafluoro-2-propanol and 10.1 g (0.1 mol) of triethylamine in 50 ml of dry diethyl ether was added dropwise with stirring at a temperature of 20° C. to a solution of 20 g (0.184 mol) of α-fluoroacryloyl chloride (obtained according to Example 4) in 50 ml of dry diethyl ether in the course of 35 minutes. The reaction mixture was then stirred at a temperature of 20° C. for a further 3.5 hours. The resulting solid was filtered off. The filtrate was distilled under reduced pressure after addition of 0.01 g of hydroquinone monomethyl ether. 17.7 g (51 percent of theory) of 2-(3,4-dimethylphenyl)-hexafluoro-2-propyl α-fluoroacrylate having a boiling point of 72° to 73° C. (under 0.4 mbar) were obtained.

EXAMPLE 11

A solution of 20 g (0.085 mol) of hexafluoro-2-(2-furyl)-2-propanol and 8.65 g (0.085 mol) of triethylamine in 25 ml of dry diethyl ether was added dropwise with stirring at a temperature of 20° C. to a solution of 9.8 g (0.09 mol) of α-fluoroacryloyl chloride (obtained according to Example 4) in 25 ml of dry diethyl ether in the course of 30 minutes. The reaction mixture was then stirred at a temperature of 20° C. for a further 4 hours. The resulting solid was filtered off. The filtrate was distilled under reduced pressure after addition of 0.005 g of hydroquinone monomethyl ether. 15.9 g (61 percent of theory) of hexafluoro-2-(2-furyl)-2-propyl α-fluoroacrylate having a boiling point of 55° to 57° C. (under 8 mbar) were obtained.

EXAMPLE 12

A solution of 20 g (0.08 moo of hexafluoro-2-(2-thienyl)-2-propanol and 8.1 g (0.08 mol) of triethylamine in 25 ml of dry diethyl ether was added dropwise with stirring at a temperature of 20° C. to a solution of 9.8 g (0.09 mol) of α-fluoroacryloyl chloride (obtained according to Example 4) in 25 ml of dry diethyl ether in the course of 30 minutes. The reaction mixture was then stirred at a temperature of 20° C for a further 3 hours. The resulting solid was filtered off. The filtrate was distilled under reduced pressure after addition of 0.005 g of hydroquinone monomethyl ether. 13.6 g (53 percent of theory) of hexafluoro-2-(2-thienyl)-propyl α-fluoroacrylate having a boiling point of 71° to 72° C. (under 0.5 mbar) were obtained.

EXAMPLE 13

A solution of 100 g of hexafluoroisopropyl α-fluoroacrylate (FAFP), 0.13 g of azobisisobutyronitrile (AIBN) and 0.33 g of butylmercaptan was filtered through a membrane fitter (pore width 45 nm) into a glass vessel and carefully degassed by first freezing the reaction mixture by means of liquid nitrogen and then evacuating the glass vessel (0.001 mbar) and warming it to room temperature, and repeating this process five times. The glass vessel was then seated and the degassed reaction mixture was first heated at a temperature of 60° C. for 3 hours and then at a temperature of 80° C. for 4 hours. Cooling down the reaction mixture to room temperature gave a glass-clear polymer material which was found to have the following properties:

| | |
|---|---|
| Average molecular mass: | 150,000 |
| Glass transition temperature: | 108.5° C. |
| Decomposition temperature: | 250° C. |
| Melt index (230° C.; 3.8 kg) | 8 g/10 min |
| Residual monomer content: | 0.2% |
| Refractive index $n_D^{23}$: | 1.355 |

EXAMPLE 14

A solution of 50 g of methanol, 50 g of FAFP, 0.03 g of AIBN and 3 g of butylmercaptan was filtered and degassed analogously to Example 13 The degassed reaction mixture was then heated at a temperature of 60° C. for 20 hours. After cooling down to room temperature, the reaction mixture had added to it 400 ml of acetone, and the resulting mixture was poured into 6 l of hexane. The precipitated polymer was separated from the liquid and was dried at a temperature of 70° C. for 6 hours. This gave 40 g (80 percent of theory) of a polymer which was found to have the following properties:

| | |
|---|---|
| Average molecular weight: | 10,000 |
| Glass transition temperature: | 102° C. |
| Decomposition temperature: | 250° C. |

EXAMPLES 15 to 20

Solutions of different amounts of FAFP and methyl methacrylate (MMA) containing in each case 0.1 g of AIBN and 0.15 g of butylmercaptan were filtered and degassed analogously to Example 13. The degassed reaction mixtures were each heated at a temperature of 60° C. for 30 min and, after cooling down to room temperature, had 300 ml of acetone added. The mixtures obtained in each case were poured into 5 l of hexane, and the precipitated copolymers were separated from the liquid and were dried at a temperature of 70° C. for 6 hours.

The respective compositions of the monomer mixture and of the copolymer and the glass transition temperature (Tg) of the copolymer can be seen in Table 1.

TABLE 1

| Example | Weight ratio MMA:FAFP | | Tg (°C.) |
|---------|---------|---------|---------|
| | Monomer mixture (g) | Copolymer (%) | |
| 15 | 85:15 | 70:30 | 119 |
| 16 | 71:29 | 58:42 | 110 |
| 17 | 48:52 | 43:57 | 107 |
| 18 | 38:62 | 38:62 | 105 |
| 19 | 29:71 | 34:66 | 103 |
| 20 | 17:83 | 28:72 | 97 |

EXAMPLE 21 to 23

Solution of different amounts of FAFP and methyl α-fluoroacrylate (FAM) containing in each case 0.1 g of AIBN and 0.15 g of butylmercaptan were filtered and degassed analogously to Example 13. The degassed reaction mixtures were each heated at a temperature of 60° C. for 30 min and, after cooling down to room temperature, had 300 ml of acetone added. The mixtures obtained in each case were poured into 5 l of hexane, and the precipitated copolymers were separated from the liquid and were dried at a temperature of 70° C. for 6 hours.

The respective compositions of the monomer mixture and of the copolymer and the glass transition temperature of the copolymer can be seen in Table 2.

TABLE 2

| Example | Weight ratio FAM:FAFP | | Tg (°C.) |
|---------|---------|---------|---------|
| | Monomer mixture (g) | Copolymer (%) | |
| 21 | 32:68 | 21:79 | 133 |
| 22 | 52:48 | 34:66 | 142 |
| 23 | 74:26 | 55:45 | 140 |

What is claimed is:

1. A process for preparing the α-fluoroacrylic acid ester $CH_2=CF-CO-O-C(CF_3)_2-R$, in which R denotes a hydrogen atom, a deuterium atom, a hologen atom, an aliphatic radical having 1 to 4 carbon atoms or an aromatic radical having 4 to 10 carbon atoms, which comprises incrementally reacting in a first process step a dimethyl α-fluoromalonate with formaldehyde, paraformaldehyde, hexmethylenetriamine or 1,3,5-trioxane, then in a second process step subjecting the resulting hydroxymethylated dimethyl α-fluoromalonate to hydrolysis, decarboxylation and dehydration and subsequently, in a third process step, esterifying the resulting α-fluoroacrylic acid, optionally after conversion to an acid halide, with an alcohol of the formula (3)

$$HO-C(CF_3)_2-R, \qquad (3)$$

in which R has the meaning previously indicated, optionally int he form of an alkali metal alcoholate.

2. The process as claimed in claim 1, wherein the first process step is carried out at a temperature of 5° to 40° C., the second process step at a temperature of 90° to 110° C. and the third process step at a temperature of 0° to 30° C.

3. The process as claimed in claim 1, wherein said α-fluoroacrylic acid or a slat thereof is converted to the corresponding acid halide, and the resulting acid halide is esterified in said esterifying step to obtain the α-fluoroacrylic acid ester.

4. The process as claimed in claim 3, wherein said corresponding acid halide is α-fluoroacryloyl chloride.

5. The process as claimed in claim 4, wherein the α-fluoroacryloyl chloride is obtained by reacting α-fluoroacrylic acid with thionyl chloride.

6. The process as claimed in claim 3, wherein the acid halide is esterified in the presence of an organic base, and the resulting α-fluoroacrylic acid ester is isolated from the reaction mixture by distillation.

7. The process as claimed in claim 1, wherein said alcohol of formula (3) is in the form of the corresponding alkali metal alcoholate.

8. The process as claimed in claim 1, wherein the resulting α-fluoroacrylic acid ester is isolated from the reaction mixture by distillation.

9. The process as claimed in claim 1, wherein the first process step is carried out at 5° to 30° C.

10. The process as claimed in claim 1, wherein, in said first process stage, the hydroxymethylated dimethyl α-fluoromalonate is isolated from the first-step reaction mixture as a solid.

11. The process as claimed in claim 10, wherein said solid is isolated form the first-step reaction mixture by one or more of the following process steps: precipitation, salting out, or extraction with a water-immiscible organic solvent.

12. The process as claimed in claim 1, wherein, in the first process step, the dimethyl α-fluoromalonate is reacted with aqueous formaldehyde in the presence of a basic catalyst.

* * * * *